(12) United States Patent
Peyman et al.

(10) Patent No.: US 7,678,078 B1
(45) Date of Patent: Mar. 16, 2010

(54) INTRAVITREAL INJECTION DEVICE, SYSTEM AND METHOD

(75) Inventors: Gholam A. Peyman, Sun City, AZ (US); Michel Jean Noel Cormier, Mountain View, CA (US); Kamran Hosseini, Los Altos, CA (US)

(73) Assignee: KMG Pharma LLC, Mountain View, CA (US)

( * ) Notice: Subject to any disclaimer, the term of this patent is extended or adjusted under 35 U.S.C. 154(b) by 0 days.

(21) Appl. No.: 12/288,510

(22) Filed: Oct. 21, 2008

(51) Int. Cl.
*A61M 5/00* (2006.01)
(52) U.S. Cl. .................................. 604/117; 604/116
(58) Field of Classification Search ................ 604/521, 604/68, 116, 117
See application file for complete search history.

(56) References Cited

U.S. PATENT DOCUMENTS

| | | |
|---|---|---|
| 5,304,128 A | 4/1994 | Haber et al. |
| 6,746,429 B2 * | 6/2004 | Sadowski et al. ............ 604/201 |
| 2003/0060763 A1 * | 3/2003 | Penfold et al. ............... 604/116 |
| 2006/0271025 A1 * | 11/2006 | Jones et al. ..................... 606/4 |
| 2007/0005016 A1 | 1/2007 | Williams |
| 2009/0036827 A1 * | 2/2009 | Cazzini ......................... 604/60 |

FOREIGN PATENT DOCUMENTS

| | | |
|---|---|---|
| EP | 0 996 447 B1 | 5/2000 |
| WO | PCT/DK98/00292 | 1/1999 |

* cited by examiner

*Primary Examiner*—Kevin C Sirmons
*Assistant Examiner*—Elizabeth R Moulton
(74) *Attorney, Agent, or Firm*—Francis Law Group

(57) ABSTRACT

An intravitreal injection device for administering a pharmacological agent formulation to an intravitreal compartment of an eye, comprising (i) a nozzle member having an internal formulation chamber that is adapted to receive and contain the pharmacological agent formulation therein, (ii) a microneedle having a first end that is in communication with the nozzle member and a second ejection end, (iii) and piercing depth limiter means for limiting the penetration depth of the microneedle into the eye, the microneedle piercing depth limiter means including guide means for positioning the limiter means and guiding the microneedle.

23 Claims, 10 Drawing Sheets

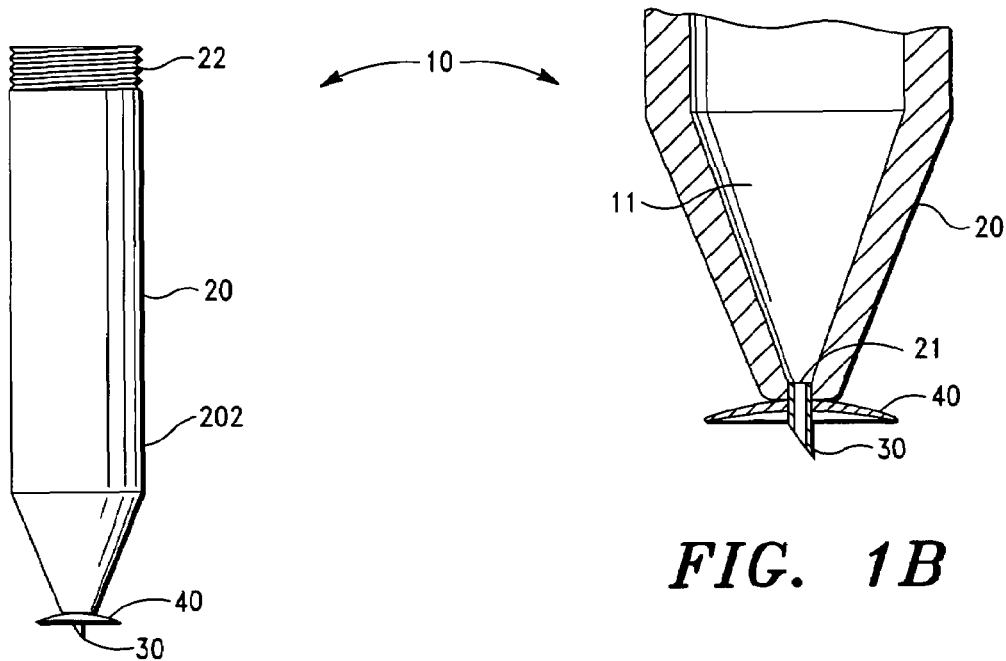
FIG. 1A
FIG. 1B
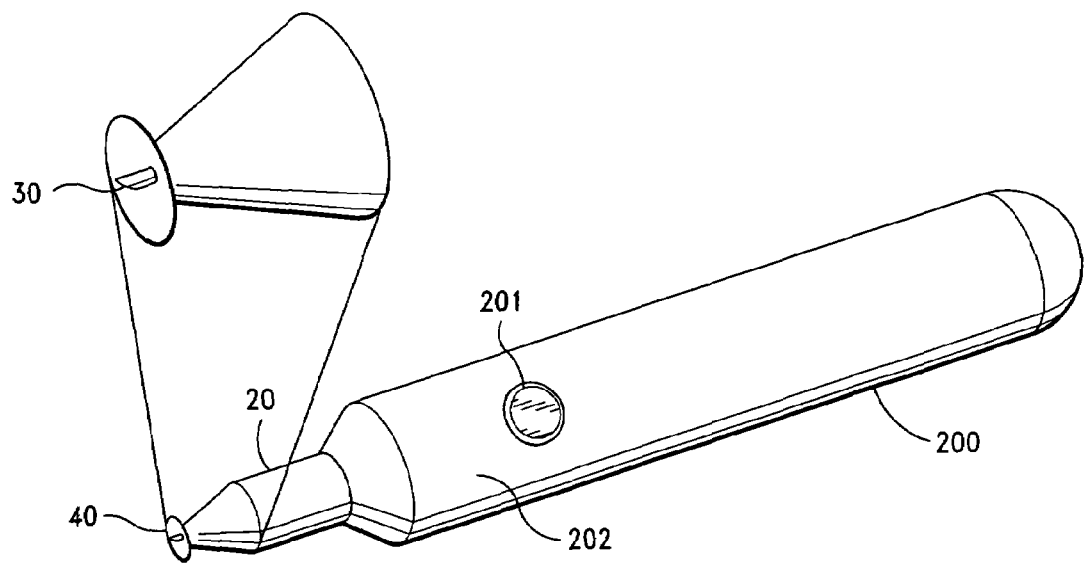
FIG. 1C

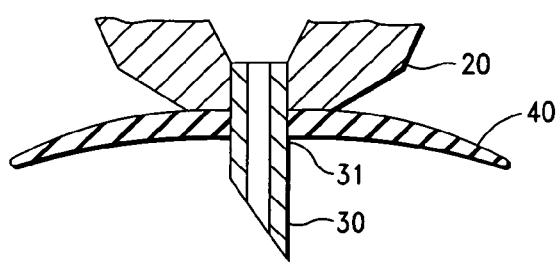 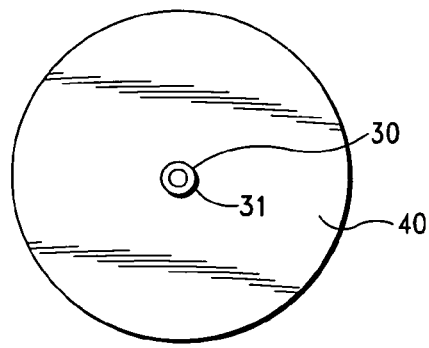
*FIG. 3A*    *FIG. 3B*
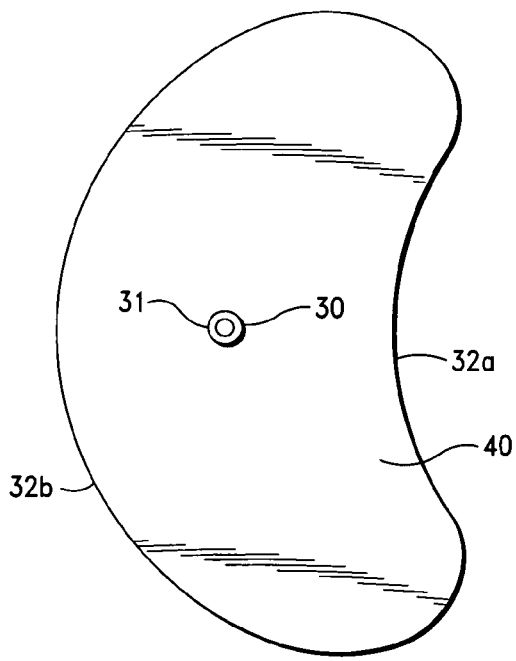 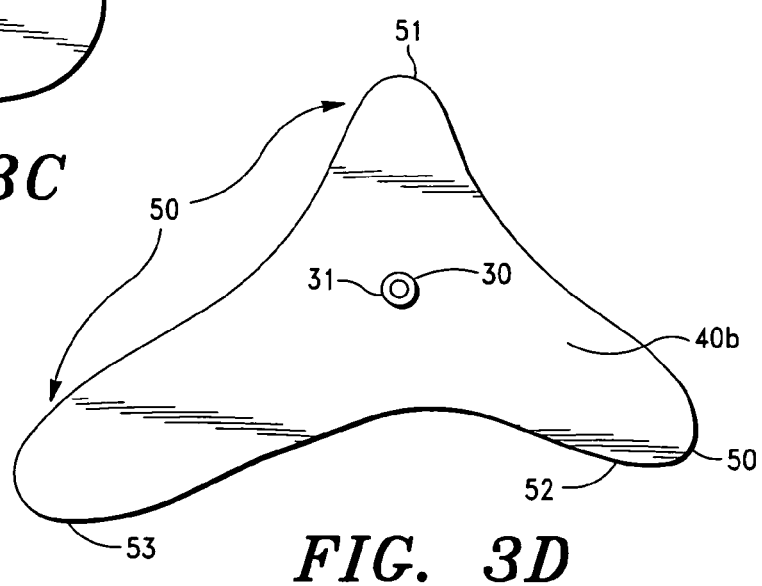
*FIG. 3C*    *FIG. 3D*

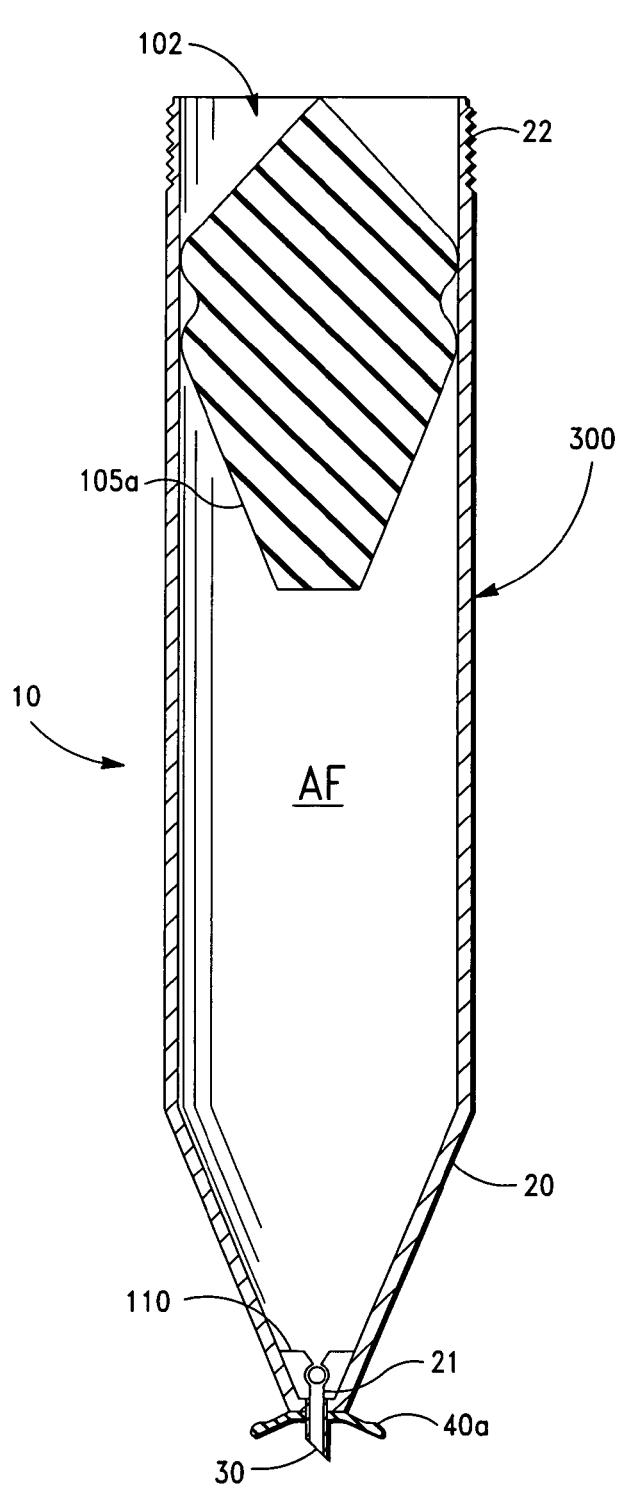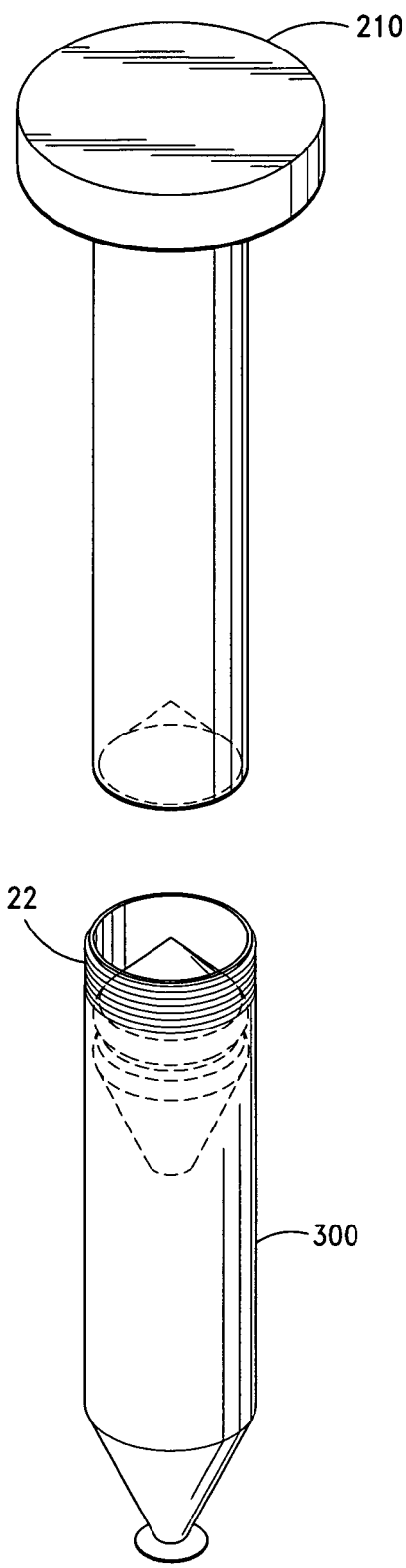
FIG. 7A
FIG. 7B

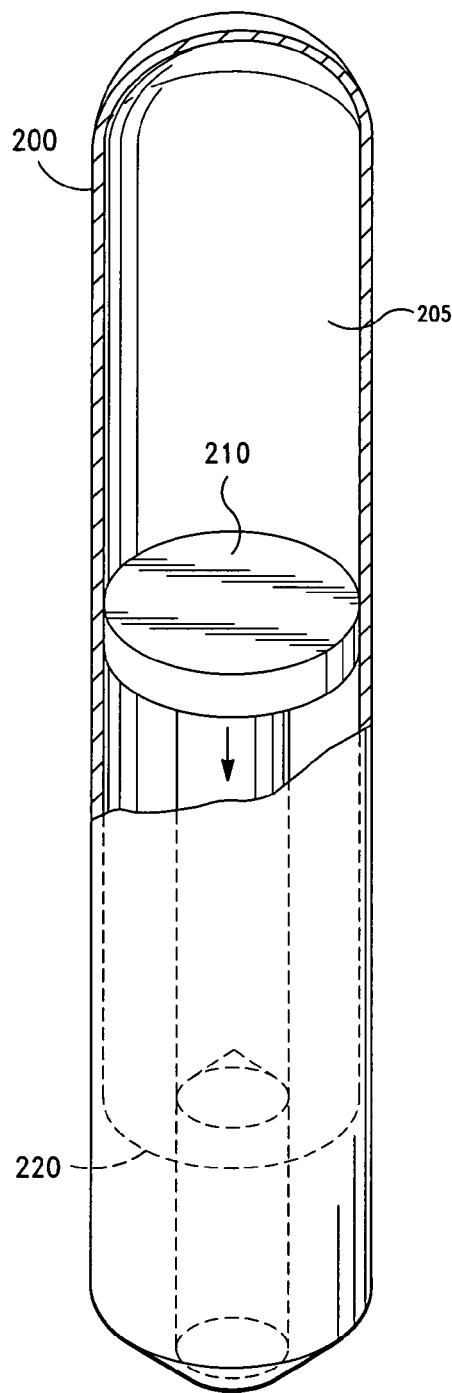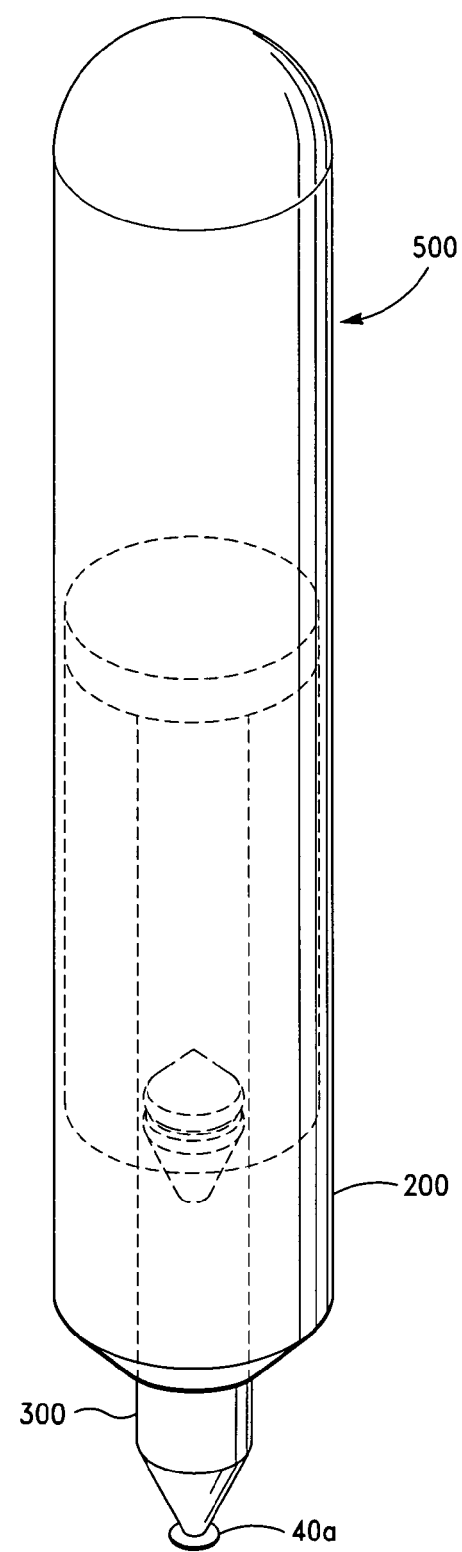
*FIG. 8A*
*FIG. 8B*

INTRAVITREAL INJECTION DEVICE, SYSTEM AND METHOD

FIELD OF THE INVENTION

This invention relates generally to intravitreal injection as a means of treating various conditions of the eye. More particularly, the invention relates to improved means for performing an intravitreal injection with the benefits of improved safety for the patient and increased efficiency for the practitioner.

BACKGROUND OF THE INVENTION

As is well known in the art, delivery of pharmacological agents (or drugs) to a specific organ or tissue can be achieved through systemic or local administration. In systemic administration, the agent is introduced into the systemic, or general, circulation by ingestion, injection, inhalation or transdermal administration. Circulating blood delivers the agent to the target tissue by either passive or active transport.

Advantages of systemic administration are that this mode of administration, especially by ingestion, is simple and well accepted by the patient. A disadvantage, however, is that the agent must be administered at relatively high doses in order to reach the target area in sufficient quantity. Moreover, the agent is delivered to the entire body, which can include sites where the agent can cause significant side effects. This is especially true for chemotherapeutic agents that tend to present significant systemic toxicity, and steroids, which present significant long-term systemic side effects.

Another significant disadvantage of systemic administration is that transfer of many pharmacological agents from the blood to certain tissues, such as the brain or an eye, is very inefficient.

An alternative to systemic administration is to administer the pharmacological agent(s) into a target organ (or tissue) or in close proximity thereto. However, as is well known in the art, local administration of an agent into or proximate an organ; particularly, an eye, typically requires strict adherence to numerous safeguards.

As discussed in detail herein, the eye is a delicate sensory organ that is surrounded by specialized structures and protected by the orbit bones, soft tissues and eyelids. The eye itself is composed of three primary layers: the sclera, the uvea, and the retina. The iris, ciliary body and choroid constitute the uvea.

Blood is transmitted through the choroid and the central retinal artery to the retina. The intraocular pressure (IOP) therein is normally below approximately 20 mm Hg. As is well known in the art, significant elevation of the IOP can, and in many instances will, collapse the choroidal and, subsequently, the retinal circulation. A long standing pressure rise can also cause rapid blindness.

Because of the complex nature of the eye, it is susceptible to a large number of abnormalities (and/or diseases). The abnormalities include dry eye, allergies, infections, various inflammatory diseases and glaucoma.

Treatments of the abnormalities and diseases have, in general, been limited to topical administration of agents or preparations. A conventional example of topical administration of an agent to the eye is the delivery of timolol via eye drops.

As is well known in the art, eye drops facilitate transmission of the agent directly to the anterior part of the eye by instillation into the cul-de-sac. The agents are then moved via the tears of the eye across the cornea and sclera into the anterior and posterior chambers of the eye without initially entering the systemic circulation path.

The advantage of this mode of administration (or delivery) is that the agent is concentrated in the target tissue with a much lower systemic exposure. This tends to reduce the above-mentioned systemic effects.

A disadvantage of this mode of administration is that not all eye tissues are accessible by this route of delivery. Tears can also redirect a significant portion of the agent away from the target area relatively quickly.

A further disadvantage of this mode of administration is that it is mostly applicable to small molecular weight pharmacological agents. Indeed, large molecular weight agents, such as antibodies, are known to diffuse poorly across the cornea or the sclera.

More recently, intravitreal injection methods and systems have been employed to administer pharmacological agents to the eye to abate abnormalities, such as macular degeneration, diabetic retinopathy and posterior uveitis. The noted agents include steroids, for which long-term systemic side effects are significant, as well as antibodies, which are known to diffuse poorly from the blood into the eye tissues.

Illustrative are the intravitreal injection methods and systems disclosed in U.S. Pat. Pub. Nos. 2003/0060763 A1 and 20070005016 A1. In U.S. Pat. Pub. No. 2003/0060763 an intravitreal injection method and system is disclosed having a plaque containing guide means for location of a needle entry point into the eye, which thereby facilitates such injection. According to the disclosure, the plaque conforms generally to the shape of the cornea and is maintained in place on the eye via contact with the eyelids. Injection occurs though a guide within the plaque via a conventional needle and syringe.

In U.S. Pat. Pub. No. 2007/0005016 another intravitreal injection method and device is disclosed that is adapted to perform injection of an agent formulation into the pars plana portion of the eye using a conventional needle and syringe. The noted publication does not, however, disclose any means of safely securing the device to the eye during injection of the agent formulation.

Although the noted intravitreal injection methods and systems represent an improvement over conventional injection with a needle and/or syringe, there are several disadvantages and shortcomings associated therewith. A major drawback is that the methods and systems disclosed in the noted references, as well as known prior art intravitreal injection methods and systems, do not provide means to properly secure the plate or the frame on the eye.

The noted intravitreal injection methods and systems also require a number of steps following the placement of the device on the surface of the eye. Further, and most importantly, the prior art intravitreal injection methods and systems employ conventional syringes and needles, which require complete penetration of the sclera and manual, non automatic, injection.

Even more recently, intraocular injection using needleless jet injection has been employed to administer pharmacological agents to the eye. Illustrative are the methods and systems disclosed in U.S. Pat. Pub. Nos. 2007/0052139, 2007/0055199, 2007/0055200 and 2007/0055214. There are, however, similarly several disadvantages and drawbacks associate with the disclosed methods and systems. A major disadvantage is that they do not include a transfer mechanism for safe, accurate, consistent, and fast injection of pharmacological agents into the intravitreal compartment of the eye.

Associated with the development of new pharmacological treatments for retinal diseases, vitreoretinal specialists are being faced with the responsibility for providing an ever increasing number of intravitreal injections of pharmacological agents and, hence, addressing the aforementioned issues associated with the prior art intravitreal injection methods and systems. There is also no universally accepted standard process for performing an intravitreal injection.

Further, intravitreal injections cannot always be scheduled in advance and each injection requires several steps to prepare the eye and safely perform the injection. The time required to perform injections can thus disrupt office schedules, resulting in unexpected prolongation of patient waiting times.

Therefore, a method and device to standardize and simplify the intravitreal injection process, improve patient comfort and safety, and increase efficiency of the process is desired.

It is therefore an object of the present invention to provide an intravitreal injection method and system that provides safe, accurate, consistent, and rapid injection of therapeutic agents into the intravitreal compartment of the eye.

It is another object of the present invention to provide an intravitreal injection method and system that facilitates injection of therapeutic agents into the intravitreal compartment of the eye with minimal risk of trauma to the patients' eye by the delivery system.

It is another object of the present invention to provide an intravitreal injection method and system that facilitates injection of therapeutic agents into the intravitreal compartment of the eye with minimal risk of trauma produced by jet formation inside the eye.

It is another object of the present invention to provide an intravitreal injection method and system that facilitates injection of agents into the subconjunctival, subtenon spaces or intrascleral and subchoroidal space.

It is another object of the present invention to provide an intravitreal injection method and system that facilitates injection of therapeutic agents into the intravitreal compartment of the eye with minimal risk of infection to the patient.

It is another object of the present invention to provide an intravitreal injection method and system that provides semi-automated injection of therapeutic agents into the intravitreal compartment of the eye.

SUMMARY OF THE INVENTION

In accordance with the above objects and those that will be mentioned and will become apparent below, in one embodiment of the invention, there is disclosed an intravitreal injection device for administering a pharmacological agent formulation to an intravitreal compartment of an eye, comprising (i) a nozzle member having an internal formulation chamber that is adapted to receive and contain the pharmacological agent formulation therein, (ii) a microneedle having a first end that is in communication with the nozzle member and a second ejection end, (iii) and piercing depth limiter means for limiting the penetration depth of the microneedle into the eye, the microneedle piercing depth limiter means including guide means for guiding the microneedle.

In a preferred embodiment of the invention, the device is adapted to engage and cooperate with a jet injector, the jet injector having force generating means that is adapted to generate sufficient force to expel the pharmacological agent formulation from the nozzle member and through the microneedle.

In one embodiment of the invention, the microneedle has a penetrating length in the range of approximately 0.1-1.0 mm, an outer diameter in the range of approximately 0.5-0.05 mm and an inner diameter in the range of approximately 0.25-0.025 mm.

In one embodiment of the invention, the piercing depth limiter means comprises a platform having an eye contact surface that substantially conforms to the surface of a sclera of the eye.

In one embodiment of the invention, the platform includes suction means that provides an engagement force when the platform is positioned on the eye.

In one embodiment of the invention, the platform has a substantially circular shape.

In one embodiment of the invention, the platform has a substantially crescent shape.

In one embodiment of the invention, the platform is substantially star shaped and includes a plurality of arms.

In one embodiment of the invention, the platform includes a plurality of suction cups disposed on the eye contact surface, the suction cups providing an engagement force when the platform is positioned on the eye.

In one embodiment of the invention, the platform includes at least one suction ring disposed on the eye contact surface.

In accordance with another embodiment of the invention, there is disclosed an intravitreal injection system, comprising (i) a transfer mechanism, the transfer mechanism including a nozzle member, a microneedle and a guide platform, the nozzle member having an internal formulation chamber that is adapted to receive and contain a pharmacological agent formulation therein, the microneedle having a first end that is in communication with the nozzle member and a second ejection end, the platform having an eye contact surface that substantially conforms to the surface of a sclera of an eye, and (ii) a jet injector having force generating means that is adapted to generate sufficient force to expel the pharmacological agent formulation from the nozzle member and through the microneedle.

In one embodiment of the invention, the volume of the pharmacological agent formulation is in the range of approximately 0.025-0.2 ml.

In one embodiment of the invention, the microneedle has a penetrating length in the range of approximately 0.1-1.0 mm.

In one embodiment of the invention, the microneedle has an outer diameter in the range of approximately 0.5-0.05 mm and an inner diameter in the range of approximately 0.25-0.025 mm.

In one embodiment of the invention, the jet injector provides an injection pressure in the range of approximately 50-1000 psi.

In one embodiment of the invention, the platform includes suction means that provides an engagement force when the platform is positioned on the eye.

In one embodiment of the invention, the platform has a thickness in the range of approximately 0.1-2.0 mm.

In one embodiment of the invention, the platform has a substantially circular shape.

In one embodiment of the invention, the circular shaped platform has a diameter in the range of approximately 4.0-8.0 mm.

In one embodiment of the invention, the platform has a substantially crescent shape.

In one embodiment of the invention, the platform is substantially star shaped and includes a plurality of arms.

In one embodiment of the invention, the platform has three arms, each of the arms having a different length.

In one embodiment of the invention, the platform includes a plurality of suction cups disposed on the eye contact surface, each of the suction cups providing an engagement force when the platform is positioned on the eye.

In one embodiment of the invention, the platform includes four suction cups.

In one embodiment of the invention, the platform includes at least one suction ring disposed on the eye contact surface.

In one embodiment of the invention, the system includes a formulation cartridge that is adapted to contain the pharmacological agent formulation, the cartridge being adapted to be slideably received in the internal formulation chamber of the nozzle member.

In accordance with another embodiment of the invention, there is disclosed a method for administering a pharmacological agent formulation to an intravitreal compartment of an eye, comprising the steps of (i) providing an intravitreal injection system having a transfer mechanism and a jet injector, the transfer mechanism including a nozzle member, a microneedle and a guide platform, the nozzle member containing the pharmacological agent formulation in an internal formulation chamber, the microneedle having a first end that is in communication with the nozzle member and a second ejection end, the microneedle having a penetrating length in the range of approximately 0.1-1.0 mm, the platform having an eye contact surface that substantially conforms to the surface of a sclera of the eye and suction means that provides an engagement force when the platform is positioned on the eye, the platform further having a substantially crescent shape, the crescent shaped platform having a concave edge and a centrally located lumen that is adapted to receive the microneedle therethrough, the jet injector having force generating means that is adapted to generate sufficient force to expel the pharmacological agent formulation from the nozzle member and through the microneedle, (ii) coupling the intravitreal injection system to the jet injector, whereby an intravitreal injection assembly is formed, (iii) positioning the intravitreal injection assembly on the pars plana area of the eye by mating the concave edge of the crescent shaped platform proximate the junction of the cornea and sclera of the eye, and (iv) activating the injector, whereby the pharmacological agent formulation is expelled from the nozzle member, through the microneedle and into the intravitreal compartment of the eye.

In one embodiment of the invention, the intravitreal injection assembly is positioned on the pars plana area of the eye by mating the concave edge of the crescent shaped platform proximate the junction of the cornea and corneoscleral limbus of the eye.

In one embodiment of the invention, the volume of the pharmacological agent formulation is in the range of approximately 0.025-0.2 ml.

In one embodiment of the invention, the jet injector provides an injection pressure in the range of approximately 50-1000 psi.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 1A is a front plan view of one embodiment of a transfer mechanism, according to the invention;

FIG. 1B is a partial cross-sectional, front plane view of the transfer mechanism shown in FIG. 1A, according to the invention;

FIG. 1C is a perspective view of one embodiment of an intravitreal injection system, according to the invention;

FIG. 3A is a partial cross-sectional, front plane view of the transfer mechanism shown in FIG. 1A, according to the invention;

FIG. 3B is a bottom plane view of one embodiment of a transfer mechanism platform, according to the invention;

FIG. 3C is a bottom plane view of another embodiment of a transfer mechanism platform, according to the invention;

FIG. 3D is a bottom plane view of a further embodiment of a transfer mechanism platform, according to the invention;

FIG. 7A is a cross-sectional, front plane view of a disposable nozzle assembly containing an agent formulation, according to the invention;

FIG. 7B is a perspective view of the disposable nozzle assembly shown in FIG. 7A, according to the invention;

FIG. 8A is a partial cross-sectional, perspective view of one embodiment of a jet injector assembly, according to the invention;

FIG. 8B is a perspective view of the disposable nozzle assembly shown in FIG. 7B operatively connected to the jet injector shown in FIG. 8A, according to the invention;

DETAILED DESCRIPTION OF THE PREFERRED EMBODIMENTS

Figure 2:
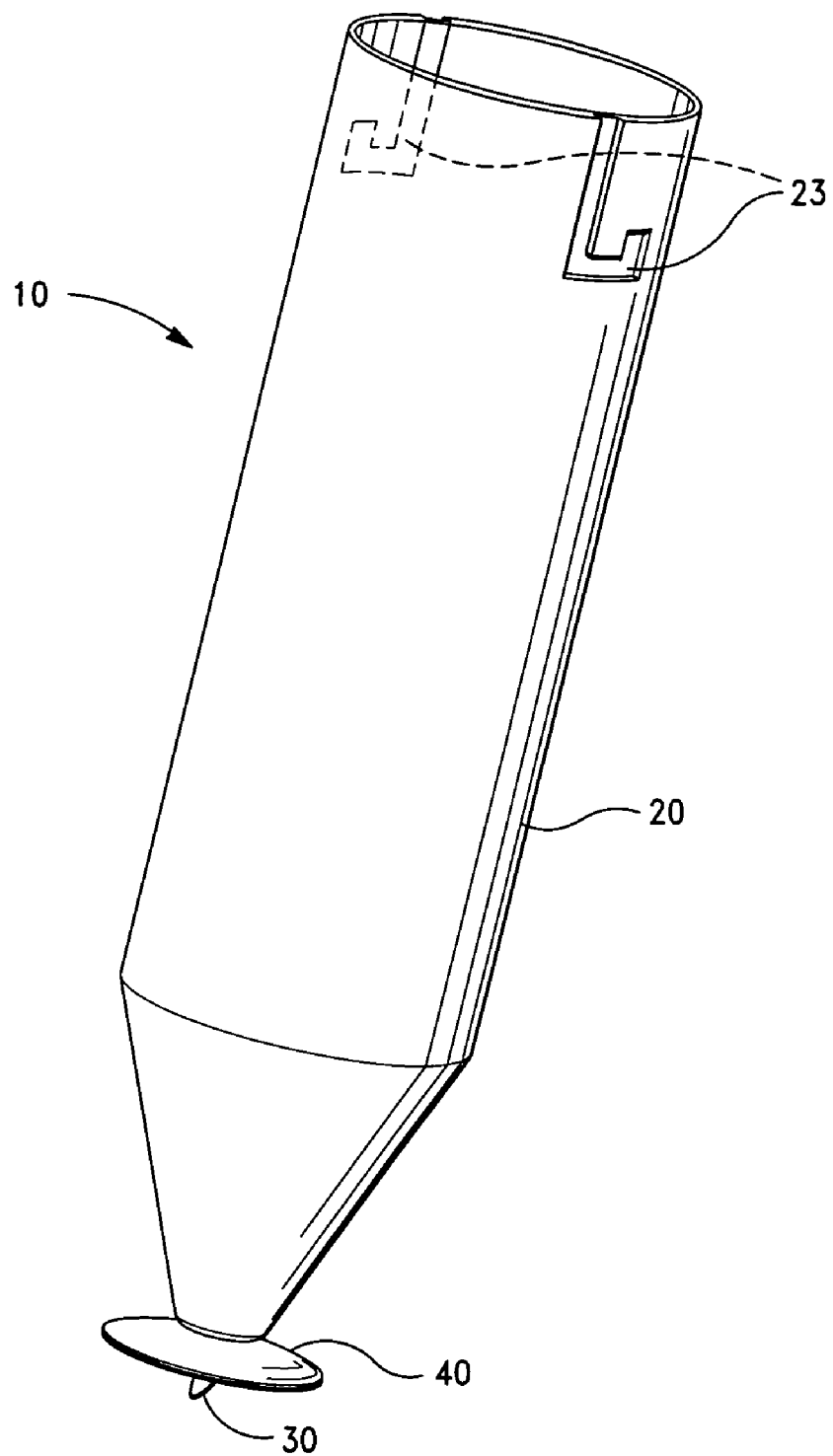
FIG. 2 is a perspective view of another embodiment of a transfer mechanism, according to the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred materials and methods are described herein.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "pharmacological agents" includes two or more such agents and the like.

DEFINITIONS

The terms "pharmacological agent", "pharmaceutical agent", "agent", "active agent", "drug", and "pharmaceutical composition" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals such as cats, dogs, sheep, goats, cattle, horses and pigs; laboratory animals such as mice, rats and guinea pigs; fish; reptiles; zoo and wild animals; and the like. The active drug that can be delivered includes inorganic and organic compounds.

According to the invention, suitable agents can be selected from, for example, small molecules, such as steroids and NSAIDs, proteins, enzymes, hormones, oligonucleotides, polynucleotides, nucleoproteins, modified DNA and RNA loaded viruses with modified capsid, polysaccharides, glycoproteins, lipoproteins, polypeptides, including drug carriers, such as pokymers, micro and nano particles.

Further examples of agents useful in this invention include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), NT-3, NT-4, NGF, IGF-2, antibiotics or antifungal drugs, anti-pain medication, anesthetics, and combinations thereof.

It is to be understood that more than one agent can be combined or mixed together and incorporated into or used by the present invention, and that the use of the term "pharmacological agent", "pharmaceutical agent", "agent", "active agent", "drug" or "pharmaceutical composition" in no way excludes the use of two or more such "pharmacological agents", "pharmaceutical agents", "agents", "active agents", "drugs", and "pharmaceutical compositions."

The terms "active agent formulation", "pharmacological agent formulation" and "agent formulation", as used herein, mean and includes an active agent optionally in combination with one or more pharmaceutically acceptable carriers and/or additional inert ingredients. According to the invention, the formulation can be either in solution or in suspension in the carrier.

As used in this application, the term "distal" shall mean the end or direction toward the front of the microneedle and/or jet injector. The term "proximal" shall mean the end or direction toward the rear of the microneedle and/or jet injector and/or transfer mechanism.

The present invention substantially reduces or eliminates the disadvantages and drawbacks associated with prior art intravitreal injection methods and systems As discussed in detail herein, the invention is directed to novel agent delivery devices and systems, their methods of manufacture and their methods of use. The invention also provides improved means of performing intravitreal injections with the benefits of improved safety for the patient and increased efficiency for the practitioner.

The following is a brief description of the various anatomical features of the eye, which will help in the understanding of the various features of the invention:

The tear film, which baths the surface of the eye, is about 0.007 mm thick. The volume of the tear film is generally approximately 0.007 mL.

The tear film has many functions, including hydration, providing nutrients to the epithelial layers, lubrication of the eyelid, and cleaning of the surface of the eye. In addition, tear film has antibacterial properties.

The cornea, which is the transparent window that covers the front of the eye, is a lens-like structure that provides two-thirds of the focusing power of the eye. The cornea is covered by an epithelium.

The cornea is slightly oval, having an average diameter of about 12 mm horizontally and 11 mm vertically. The central thickness of the cornea is approximately 0.5 mm and approximately 1 mm thick at the periphery.

The aqueous humor occupies the anterior chamber of the eye. The humor has a volume of about 0.6 mL.

The aqueous humor provides nutrients to the cornea and lens. The humor also maintains normal IOP.

The limbus is the 1-2 mm transition zone between the cornea and the sclera. This region contains the outflow apparatus of the aqueous humor.

The conjunctiva is a thin clear vascular mucous membrane that starts at the limbus and covers the sclera and the inner surface of the eyelid. The conjunctiva is composed of non-keratinized statified columnar epithelium, which is approximately 3-7 layers thick. The average thickness of the conjunctiva is about 0.05 mm.

The conjunctiva also contains goblet cells that secrete the mucin layer of the tear film, as well as the accessory lacrimal glands of Krause and Wolfring.

The sclera is the white region of the eye, i.e. posterior five sixths of the globe. It is the tough, avascular, outer fibrous layer of the eye that forms a protective envelope. The sclera is mostly composed of dense collagen fibrils that are irregular in size and arrangement (as opposed to the cornea). The extraocular muscles insert into the sclera behind the limbus.

The sclera can be subdivided into 3 layers: the episclera, sclera proper and lamina fusca. The episclera is the most expernal layer. It is a loose connective tissue adjacent to the periorbital fat and is well vascularized.

The sclera proper, also called tenon's capsule, is the layer that gives the eye its toughness. The sclera proper is avascular and composed of dense type I and III collagen.

The lamina fusca is the inner aspect of the sclera. It is located adjacent to the choroid and contains thin collagen fibers and pigment cells.

The pars plana is a discrete area of the sclera. This area is a virtually concentric ring that is located between 2 mm and 4 mm away from the cornea. This area is devoid of the inner retinal layer, which, as discussed in detail below, makes it a prime target for intraocular injection.

The mean scleral thickness ±SD of the pars plana is reported to be approximately 0.53±0.14 mm at the corneo-scleral limbus, significantly decreasing to 0.39±0.17 mm near the equator, and increasing to 0.9 to 1.0 mm near the optic nerve. At the location of the pars plana, the thickness of the sclera is about 0.47±0.13 mm.

The thickness of the sclera is known to vary according to sex, age, and is altered in various pathological conditions. Overall, the range of thickness of the sclera at the location of the pars plana is estimated to be in the range of approximately 0.3-1.0 mm. The total thickness of the membranes enclosing the eye cavity, at the location of the pars plana, is estimated to be in the range of approximately 0.5-1 mm.

The uvea refers to the pigmented layer of the eye and is made up of three distinct structures: the iris, ciliary body, and choroid. The iris is the annular skirt of tissue in the anterior chamber that functions as an aperture. The iris root attaches to the ciliary body peripherally. The pupil is the central opening in the iris.

The ciliary body is the 6 mm portion of uvea between the iris and choroid. The ciliary body is attached to the sclera at the scleral spur. It is composed of two zones: the anterior 2 mm pars plicata, which contains the ciliary muscle, vessels, and processes, and the posterior 4 mm pars plana.

The ciliary muscle controls accommodation (focusing) of the lens, while the ciliary processes suspend the lens (from small fibers called zonules) and produce the aqueous humor (the fluid that fills the anterior and posterior chambers and maintains intraocular pressure).

The choroid is the tissue disposed between the sclera and retina. The choroid is attached to the sclera at the optic nerve and scleral spur. This highly vascular tissue supplies nutrients to the retinal pigment epithelium (RPE) and outer retinal layers.

The layers of the choroid (from inner to outer) include the Bruch's membrane, choriocapillaris and stroma. Bruch's membrane separates the RPE from the choroid and is a permeable layer composed of the basement membrane of each, with collagen and elastic tissues in the middle.

A suprachoroidal space exists between the choroid and sclera. In certain disease processes, fluid or blood can fill this space creating a choroidal detachment.

The crystalline lens, located between the posterior chamber and the vitreous cavity, separates the anterior and posterior segments of the eye. Zonular fibers suspend the lens from the ciliary body and enable the ciliary muscle to focus the lens by changing its shape.

The retina is the delicate transparent light sensing inner layer of the eye. The retina faces the vitreous and consists of 2 basic layers: the neural retina and retinal pigment epithelium. The neural retina is the inner layer. It has 9 layers, including the photoreceptor layer. The retinal pigment epithelium is the outer layer that rests on Bruch's membrane and choroid.

The vitreous is the largest chamber of the eye (i.e. ±4.5 ml). The vitreous is a viscous transparent gel composed mostly of water. It also contains a random network of thin collagen fibers, mucopolysaccharides, and hyaluronic acid.

The vitreous adheres firmly to the margin of the optic disc and to the peripheral retina at the ora serrata and the pars plana. With aging, the vitreous liquefies, a process known as syneresis.

As indicated above, the present invention provides improved means of performing intravitreal injections with the benefits of improved safety for the patient and increased efficiency for the practitioner. The intravitreal injection system, in accordance with the present invention, is adapted to deliver active agents or medicaments, such as agent formulations, to the intravitreal compartment of a patient by injecting very fine streams of the agent formulations at high velocity.

According to the invention, the agent formulations can comprise various forms, including, without limitation, liquids and powders.

As discussed in detail herein, in one embodiment of the invention, the intravitreal injection system of the invention includes a transfer mechanism having a nozzle member, microneedle and platform that is adapted to receive and guide the microneedle. Preferably, the transfer mechanism is sterilized and packaged individually for single use.

In a preferred embodiment of the invention, a jet injector is operatively connected to the transfer mechanism prior to application (or engagement) of the intravitreal injection system to the eye.

According to the invention, the microneedle provides a guide for the liquid jet stream, as well as anchoring the intravitreal injection device and/or system at the surface of the eye.

As discussed in detail below, the platform is designed to conform to the surface of the sclera and to provide a support for precise injection at the pars plana site and, in some embodiments, adhesion of the platform to the eye.

The invention is also directed to an intravitreal injection assembly or kit, which, in one embodiment of the invention, includes (1) a pharmacological formulation, i.e. active agent formulation, containing an effective amount of an agent useful for treating a condition of an eye of a patient, (2) a transfer mechanism having a nozzle member, a microneedle and a platform, and (3) a jet injector to facilitate ejection of the pharmacological formulation into and through the transfer mechanism. As indicated above, the agent formulation can comprise of various forms, such as a liquid or powders.

In one embodiment of the invention, the total volume of the active agent formulation that is provided and, hence, injected in the intravitreal space is preferably in the range of approximately 0.025-0.2 mL.

Preferably, injection into the intravitreal space is performed through a very discrete area of the eye, i.e. the pars plana. As indicated above, this area is devoid of the inner retinal layer, which makes it a prime target for intraocular injection.

As is well known in the art, the eye is an immune privileged organ and, thus, is quite susceptible to infection. Indeed, bacteria can potentially multiply as a result of the absence of vascularization of the internal cavity of the eye.

Use of conventional jet injection for ocular administration, such as disclosed in U.S. Pat. Pub. No. 2007/0055200, is therefore likely to result in an increase incidence of intraocular infection. Indeed, the jet stream creates a reduced atmospheric pressure at the interface between the surface of the eye and the jet injector nozzle which, if the seal between the nozzle and the surface of the eye is not perfect, could, in turn, result in aspiration of microorganisms present on the surface of the eye and their dispersion into the intraocular compartments.

Because of the reduced immune response of the eye, as compared to that of other organs, such as the skin, ocular infection is therefore more likely to occur with jet injection, as compared to conventional injection. Use of a needle that penetrates into the scleral membrane acts as a guide for the jet stream and creates an effective seal, excluding air and fluids present at the surface of the conjunctiva, therefore minimizing the risk for aspiration of microorganism from the surface of the eye and the subsequent risk of infection.

The retina is the most sensitive part of the eye. It is very susceptible to environment changes, including physiological changes, such as inflammation (hence its immune privileged property) or physical changes, such as changes in pressure. The retina is therefore of utmost importance to minimize changes in intraocular pressure.

As is also well known in the art, conventional jet injectors involve pressures of up to 25,000 psi (see, for example, U.S. Pat. Pub. No. 2007/0055200). Such injection pressures are generally acceptable for transdermal agent delivery. However, such jet injectors doubtless carry a risk for retinal detachment when used for intraocular drug delivery as a result of increase in intraocular pressure, which causes closure of the retinal vessels.

Use of a needle that penetrates through the conjunctiva and the scleral membrane of the eye allow a microneedle assisted jet injector to operate at lower pressure (as compared to a conventional jet injector) as a result of the reduced thickness of the barrier. The lower pressure thus minimizes the risk of retinal detachment or rise in intraocular pressure.

An additional advantage for the use of a needle in conjunction with a jet injector is that the needle provides an anchoring point that allows for more precise and safer intraocular injection at and through an area that is not covered internally by the retina (otherwise it would create a retinal tear and detachment of the retina).

Use of a conventional needleless jet injector is, however, technically challenging. If the needleless jet injector is not positioned perpendicular to the tissue interface or if a poor contact is established between the nozzle and the tissue at the time of injection, a "wet" injection may occur. A wet injection is characterized by loss of a significant fraction of the medication at the surface of the tissue and/or, in the case of the skin, injection of the medication into the dermis instead of the subcutaneous or intramuscular space.

One of the root causes for wet injection is non-perpendicularity of the nozzle with the surface of the tissue, which results in the jet contacting the surface of the tissue at an angle. This can result in reflection of all or part of the jet by the tissue surface and/or total or partial intradermal injection.

Another cause for wet injection is poor contact with the tissue, which results in dissipation of a significant fraction of the jet energy through air aspiration that may be injected concomitantly with the medication.

Although wet injection is not desirable during transdermal administration, its consequences are relatively benign and a small percentage of such failure is generally deemed acceptable.

In the case of intraocular administration, wet injection would result in significant loss of the medication at the surface of the conjunctiva, which could likely cause potential harmful consequences depending of the agent being considered. Additional potential adverse consequences include subconjunctival or/and intrascleral injection of the medication and, possibly, air/contamination entrapment, resulting in tissue damage and subsequent inflammation. In addition, a misdirected jet can also cause a retinal tear.

Wet injection would accordingly be unacceptable in the case of intraocular administration.

As will be readily appreciated by one having ordinary skill in the art, the use of a needle-assisted intravitreal injection device of the invention minimizes the risk of wet injection as a result of anchoring the transfer mechanism microneedle in the sclera.

Since the eye comprises a multi-layer tissue and a conventional needleless injector is applied to the external surface of the outermost layer, the delivery pressure must be high enough to penetrate all layers of the eye. For needleless jet injection, the required delivery pressure is typically greater than approximately 4000 psi (measured as the force of the fluid stream divided by the cross-sectional area of the fluid stream).

As mentioned above, such injection pressures, which are acceptable for transdermal agent delivery, carry a risk for retinal detachment when used for intraocular agent. However, use of a needle that only penetrates part of the scleral membrane of the eye allows jet injectors to operate at significantly lower pressure as a result of the reduced thickness of the barrier. The risk of retinal detachment is therefore minimized.

Applicants submit that in order for the jet stream to penetrate through the remaining part of the sclera, into and through the choroid and into the intravitreal cavity, a pressure of only approximately 50-1000 psi (measured as the force of the fluid stream divided by the cross-sectional area of the fluid stream) is required. The noted pressure range is dependant on a number of factors, including the depth of penetration of the injection member, e.g., needle through the sclera, the gauge of the injection member, and the volume of liquid medication to be injected.

The noted pressure range could also be lowered by using an injection member that would penetrate all the way through all the eye layers and into the intravitreal cavity. Unfortunately, injection members, such as needles, longer than about 1 mm would result in increased risk of infection and would also increase the risk of physical trauma to the internal eye tissues, such as the lens, retina, ciliary muscle and choroid. Such injection members would therefore not be desirable.

In addition, the amount of pressure required for the jet stream to penetrate into and through the remaining part of the sclera and the choroid, and into the intravitreal cavity would be difficult to set at a safe range, since the injection member is already in the eye cavity. However, partial penetration of a needle through the sclera reduces the risk of infection, as compared to full penetration through the sclera, since the external surface of the injection member that comes in contact with the ocular surface flora remains isolated from the vitreous cavity. Further, the sterile formulation is injected into the vitreous cavity without becoming contaminated with the ocular surface flora.

Accordingly, in one embodiment of the invention, the injection member of the invention, i.e. microneedle, which is described in detail below, has a length in the range of approximately 0.1-1 mm. An injection pressure in the range of approximately 50-1000 psi (measured as the force of the fluid stream divided by the cross-sectional area of the fluid stream) is also employed. The noted transfer mechanism parameter and injection pressure range offer the greatest safety for intravitreal administration.

According to the invention, the jet injector is preferably reusable and can be powered by compressed gas, pyrotechnics, electricity, or a spring, such as disclosed in U.S. Pat. Nos. 5,954,689, 5,704,911, 5,505,697, 6,585,685 and 7,150,409; which are incorporated by reference herein.

In an alternative embodiment of the invention, the jet injector is disposable, as described, for example in U.S. Pat. No. 6,682,504; which is also incorporated by reference herein. As discussed in detail below, in some embodiments, the transfer mechanism and jet injector can be preassembled and ready for use without any further assembly.

In one embodiment of the invention, the jet injector is capable of producing pressure in the range of approximately 50-1000 psi (measured as the force of the fluid stream divided by the cross-sectional area of the fluid stream).

Referring now to FIGS. 1A and 1B, there is shown one embodiment of a transfer mechanism of the invention. As illustrated in FIG. 1B, the transfer mechanism 10 includes a nozzle member 20 having an internal formulation chamber 11 that is adapted to receive a pharmacological formulation therein. The nozzle member 20 further includes an opening (or lumen) 21 at the distal end that is in communication with the formulation chamber 11 and is adapted to receive a fixed tubular insert or hollow microneedle 30. Preferably, the microneedle 30 has an outer diameter in the range of approximately 0.5-0.05 mm and an inner diameter in the range of approximately 0.25-0.025 mm.

As indicated above, in a preferred embodiment of the invention, the microneedle 30 has a penetrating length in the range of approximately 0.1-1 mm. The term "penetrating length" length refers to the actual length of the microneedle 30 that is allowed to penetrate the eye tissue. According to the invention, the actual length of the microneedle 30 can be longer than the penetrating length.

According to the invention, the microneedle 30 can comprise metal or other suitable materials, such as a ceramic or polymeric material. Further, although FIG. 1A shows a multi-piece nozzle assembly, the microneedle 30 and nozzle member 20 can comprise an integral member.

Preferably, when the microneedle 30 is a separate component it is safely secured to the nozzle member 20 to avoid accidental detachment of the microneedle 30 from the nozzle member 20 during the injection process.

Referring now to FIG. 1C, the transfer mechanism 10 is designed and adapted to be coupled to a jet injector 200. According to the invention, various conventional means can be employed to couple the transfer mechanism 10 and jet injector 200.

In one embodiment of the invention, coupling of the transfer mechanism 10 and jet injector 200 is achieved by providing external threads 22 on the end of the nozzle member 20 (see FIG. 1A) that are adapted to cooperate with corresponding threads formed on the inner wall surface of the injector body 202.

Referring now to FIG. 2, in another embodiment, a bayonet coupling 23 is provided on the end of the nozzle member 20. A mating coupling is also provided on the inner wall surface of the injector body 202 that is adapted to cooperate with the nozzle member coupling 23.

According to the invention, the nozzle member 20 can comprise various polymeric materials, metals and/or metal alloys. In one embodiment of the invention, the nozzle member 20 is constructed of a molded polymeric material, such as polyethylene, polystyrene, or polyvinyl chloride.

Figure 3E:
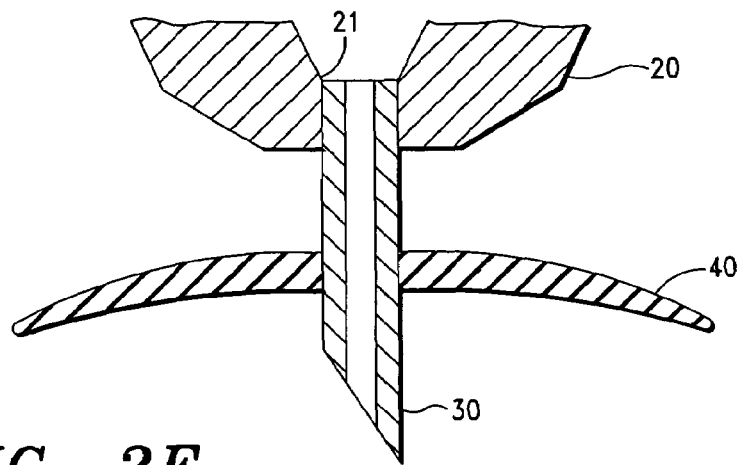
FIG. 3E is a partial cross-sectional, front plane view of another embodiment of a transfer mechanism, according to the invention.

Referring now to FIGS. 1B and 3A, in a preferred embodiment of the invention, the transfer mechanism 10 also includes a platform (in this instance, platform 40). According to the invention, the platform, e.g., platform 40, is preferably disposed proximate the distal end of the nozzle member 20, as illustrated in FIGS. 1B and 3A. In another embodiment, the platform is positioned along the shaft of the microneedle 30, as illustrated in FIG. 3E.

According to the invention, platform 40 (and platforms 40a, 40b, 40c and 40d, discussed in detail below) are designed and configured to conform to the surface of the eye, i.e. include a concave eye contact region, and can comprise various shapes. In one embodiment, which is illustrated in FIGS. 3A and 3B, the platform 40 has a substantially circular shape and includes a centrally located lumen 31 that is adapted to receive the microneedle 30 therethrough (see FIG. 3A).

In one embodiment, the platform 40 has a diameter in the range of approximately 4-8 mm. In one embodiment, the platform 40 preferably has a diameter in the range of approximately 5-8 mm.

In one embodiment, the platform 40 preferably has a diameter in the range of approximately 4-6 mm. As will readily appreciated by one having ordinary skill in the art, the noted smaller diameter platform would facilitate use with younger patients.

In another embodiment, which is illustrated in FIG. 3C, the platform 40a has a crescent or kidney shape and similarly includes a centrally located lumen 31 that is adapted to receive the microneedle 30 therethrough. In the noted embodiment, the microneedle 30 is preferably disposed approximately 2-4 mm away from the concave edge (denoted "32a") of the platform 40a.

In one embodiment of the invention, the microneedle 30 is preferably disposed orthogonal to the platform 40a. However, according to the invention, the microneedle 30 need not be disposed orthogonal to the platform 40a, but can be directed towards the convex edge of the platform 40a (denoted "32b") at an additional angle of up to 30°. The noted angular positioning reduces the risk of internal ocular injury; particularly, with regards to the lens.

Referring now to FIG. 3D, in another embodiment, the platform 40b is star shaped and includes a plurality of arms 50. In the illustrated embodiment, the platform 40b includes three arms 50 that preferably have different lengths.

In one embodiment of the invention, one of the arms 51 is preferably approximately 2 mm, the second arm 52 is preferably approximately 3 mm, and the third arm 53 is approximately 4 mm.

As will be readily appreciated by one having ordinary skill in the art, the different length arms 50 allow the practitioner to use only one transfer mechanism for children and adults.

According to the invention, the arms 50 of the star-shaped platform 40b can also be color coded or marked for easy identification.

According to the invention, the platforms of the invention, i.e. 40, 40a, 40b, and 40c and 40d (discussed below), are preferably constructed of thin (i.e. ~0.1-2 mm) and elastic, biocompatible polymeric material. Preferably, the polymeric material comprises an elastomer, such as natural rubber, polybutadiene, nitrile rubber, neoprene, silicone rubber, and ethylene vinyl acetate. In one embodiment, the platforms of the invention are constructed of a transparent polymer, such as transparent thermoplastic polyurethane elastomers.

According to the invention, at the time of intraocular injection, placement of the edge of the circular platform 40, or the concave edge 32a of the crescent-shaped platform 40a, or of the tip of one of the arms 50 of the star-shaped platform 40b, at the location of the corneoscleral limbus allows precise positioning and application of the microneedle 30 to the pars plana area.

When resting on the conjunctiva, the platforms of the invention, i.e. platforms 40, 40a, 40b, 40c, 40d, act as a piercing depth limiter for the microneedle 30 and as a soft and non-abrasive support for the jet injector, thereby eliminating guesswork by the practitioner. The noted platforms of the invention also prevent internal eye injury resulting from penetration of the microneedle 30 beyond the sclera and superficial eye injury that could result from contact of the surface of the eye with the distal end of the nozzle member of conventional jet injectors.

In addition, the platforms of the invention help assure orthogonality of the jet injector 200 relative to the surface of the eye and stabilization of the jet injector 200 at the time of injection.

In a preferred embodiment of the invention, platforms 40, 40a and 40b of the invention include suction means. According to the invention, the wet surface of the eye combined with the use of an elastic polymeric material, the concave contact region of each platform and the small size of the platform provide mild adhesive properties of the platform, e.g. platform 40, to the surface of the eye through interfacial forces. As a result, application of one of the noted platforms to the pars plana area results in an effective seal therefore further decreasing the risks for air entrapment, wet injection, and infection. In addition, this mild adhesion provides an effective supplemental means for assuring orthogonality of the jet injector relative to the surface of the eye and stabilization of the jet injector during injection.

Figure 4A:
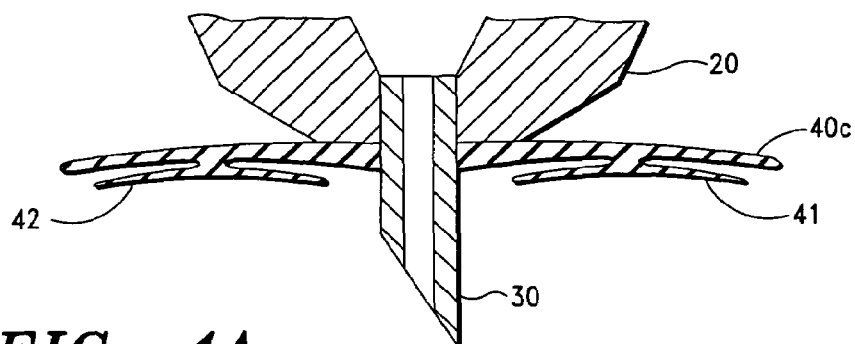
FIG. 4A is a partial cross-sectional, front plane view of another embodiment of a transfer mechanism, according to the invention.
Figure 4B:
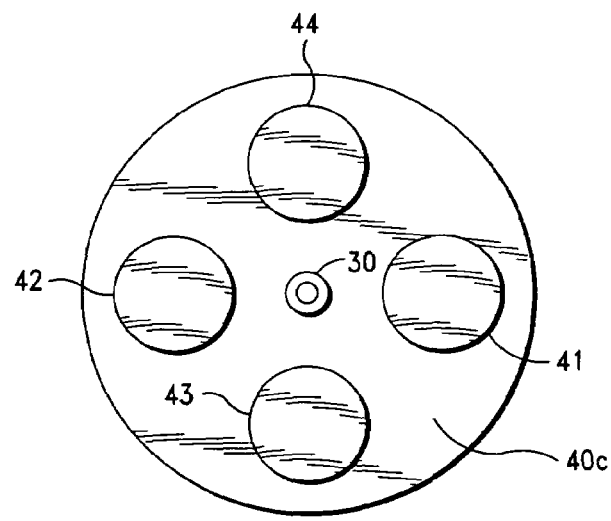
FIG. 4B is a bottom plane view of the transfer mechanism shown in FIG. 4A, according to the invention.

In another embodiment of the invention, the platform includes at least one, preferably, a plurality of suction cups. In one embodiment, which is illustrated in FIG. 4A, the platform 40c includes two suction cups 41, 42 that are disposed on the bottom of the platform 40c. In another embodiment, which is illustrated in FIG. 4B, the platform 30c includes four suction cups 41, 42, 43, 44.

In one embodiment, the suction cups 41, 42, 43, 44 are preferably constructed of the same material as the platform 40c. In another embodiment, the suction cups 41, 42, 43, 44 and platform 40c are constructed of the different materials.

According to the invention, the platform 40c can include any number of suction cups. Preferably, less than twelve suction cups are present on the platform 40c. The suction cups can also have various shapes and dimensions, and can be disposed or positioned in various patterns on the platform 40c. The suction cups can also comprise separate components or be an integral part of the platform 40c.

Figure 5A:
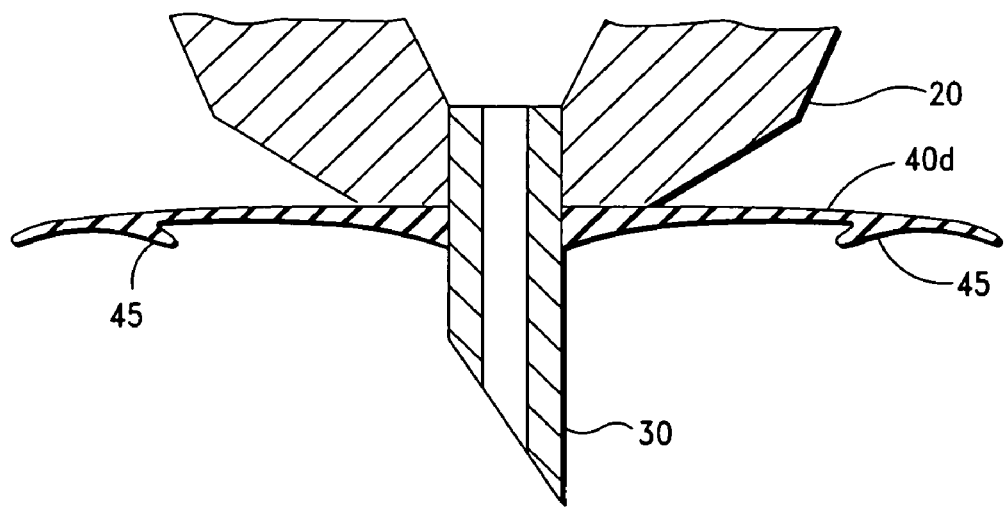
FIG. 5A is a partial cross-sectional, front plane view of another embodiment of a transfer mechanism, according to the invention.
Figure 5B:
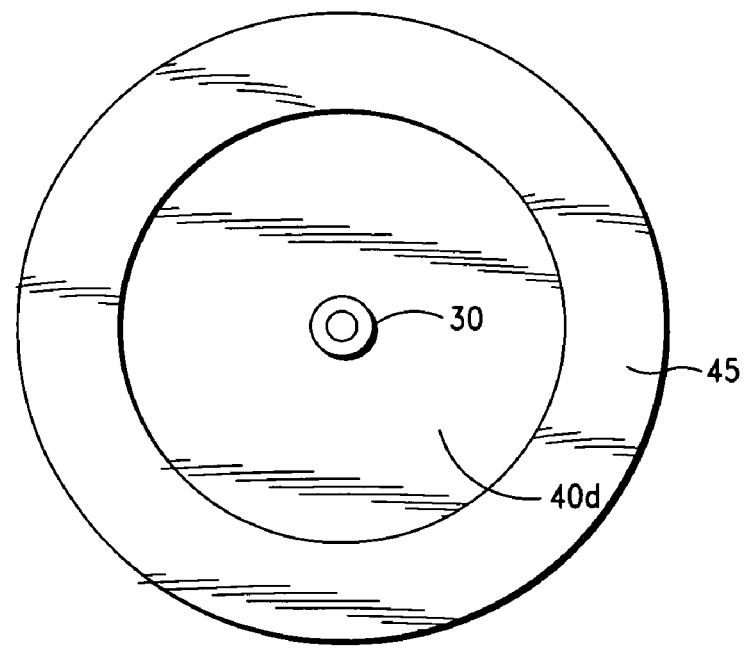
FIG. 5B is a bottom plane view of the transfer mechanism shown in FIG. 5A, according to the invention.

Referring to FIG. 5A, there is shown yet another embodiment of a platform of the invention. As illustrated in FIG. 5A, in this embodiment, the platform 40d includes at least one suction ring 45 that is disposed on the bottom of the platform 40d. Preferably, the suction ring 45 is substantially centrally positioned on the platform 40d, as illustrated in FIG. 5B.

In some embodiments of the invention (not shown), the platform 40d includes more than one suction ring 45 for optimal attachment.

According to the invention, the suction ring 45 is similarly preferably constructed of the same material as the platform 40d and can be an integral part of the platform 40d. The suction ring 45 and platform 40d can also be constructed of different materials.

Figure 6C:
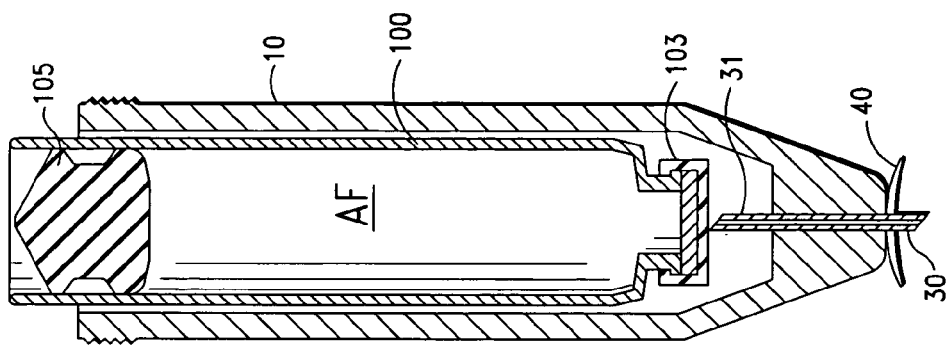
FIG. 6C is a cross-sectional, front plane view of the cartridge shown in FIG. 6B assembled with the transfer mechanism shown in FIG. 6A, according to the invention.
Figure 6B:
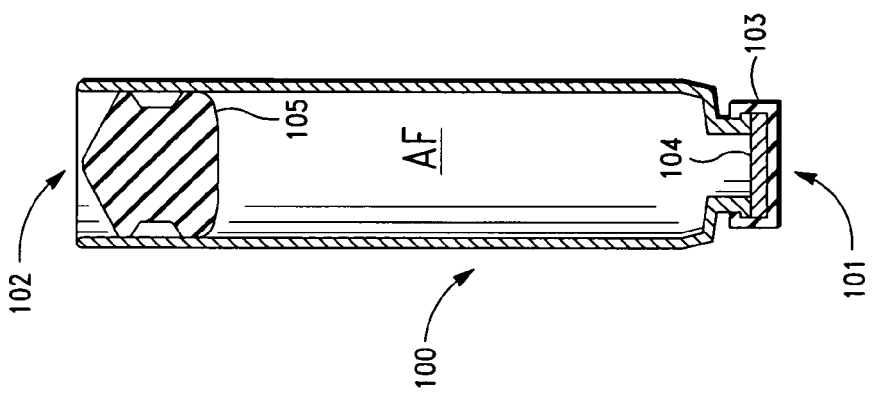
FIG. 6B is a cross-sectional, front plane view of one embodiment of a disposable cartridge, according to the invention.
Figure 6A:
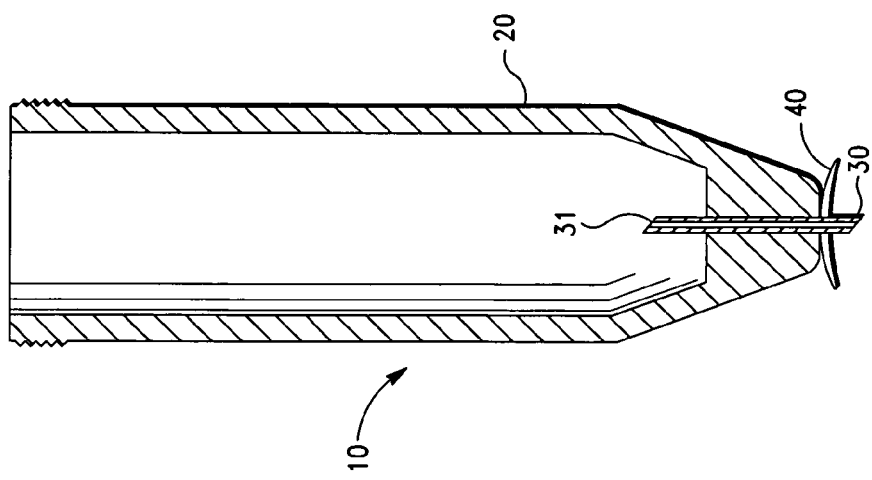
FIG. 6A is a cross-sectional, front plane view of another embodiment of a transfer mechanism, according to the invention.

Referring now to FIGS. 6A-6C, there is shown a transfer mechanism 10 and a disposable cartridge 100 being employed therewith. According to the invention, the agent formulation is preferably contained in the disposable cartridge 100 (denoted "AF").

Referring to FIG. 6B, the cartridge 100 preferably includes a distal end 101 and a proximal end 102; each end having an opening therethrough, a pierceable seal 103 that is associated with the opening in the distal end 101, and a stopper 105 that is disposed in the proximal end 102 of the cartridge 100. The stopper 105 is sized and adapted to seal the opening at the proximal end 102 of the cartridge 100 and slide within the cartridge 100.

Referring to FIG. 6A, the transfer mechanism 10 includes an injection assisted microneedle 31 that cooperates with microneedle 30. As illustrated in FIG. 6A, microneedle 31 is preferably directed toward the proximal side of the transfer mechanism 10.

According to the invention, the injection assisted needle 31 and microneedle 30 can comprise an integral component. The injection assisted needle 31 can also have the same gauge as the microneedle 30, as depicted in FIG. 6A, or can have a different gauge.

According to the invention, at the time of use, the cartridge 100 is placed inside the transfer mechanism 10, as illustrated in FIG. 6C. The cartridge 100 is then pushed manually toward the distal end of the transfer mechanism 10, whereby the injection assisting needle 31 pierces the seal 103. The assembly is then secured to the power unit of the jet injector 200. Activation of the power unit, i.e. force generating source, of the jet injector 200 (discussed below) moves the stopper 105 toward the distal end of the transfer mechanism 10, whereby the agent formulation is directed into and through the injection assisting needle 31 and microneedle 30.

In other embodiments of the invention, piercing of the seal 103 is accomplished via the action of securing the assembly, i.e. transfer mechanism 10 and cartridge 100, to the jet injector 200 or is accomplished by the force generating source of the jet injector 200.

Referring now to FIGS. 7A and 7B, there is shown one embodiment of a transfer mechanism having a disposable nozzle assembly or cartridge 300. As illustrated in FIG. 7A, the nozzle assembly 300 has an opening 21 at the distal end and another opening 102 at the proximal end thereof, a stopper 105a disposed proximate the proximal end of the nozzle assembly 300, and an outlet valve member 110 disposed proximate opening 21. The transfer mechanism 10 additionally includes a fixed microneedle 30 that is disposed proximate the distal end of the nozzle assembly 300, and a platform of the invention. In one embodiment, the platform comprises the circular shaped platform 40 illustrated in FIGS. 3A and 3B.

According to the invention, the agent formulation is preferably contained in the disposable nozzle assembly 300 between the stopper 105a and outlet valve member 110.

In some embodiments of the invention, the transfer mechanism 10 includes a breakable pressure sensitive membrane (not shown), which replaces the outlet valve member 110.

According to the invention and as illustrated in FIG. 8B, the transfer mechanism 10 with the disposable nozzle assembly 300 is similarly adapted to engage (or be coupled to) the jet injector 200 via threads 22. Following assembly, the assembled system 500 is applied to the pars plana area 410 of the eye 400, as illustrated in FIGS. 9A and 9C.

Figure 9A:
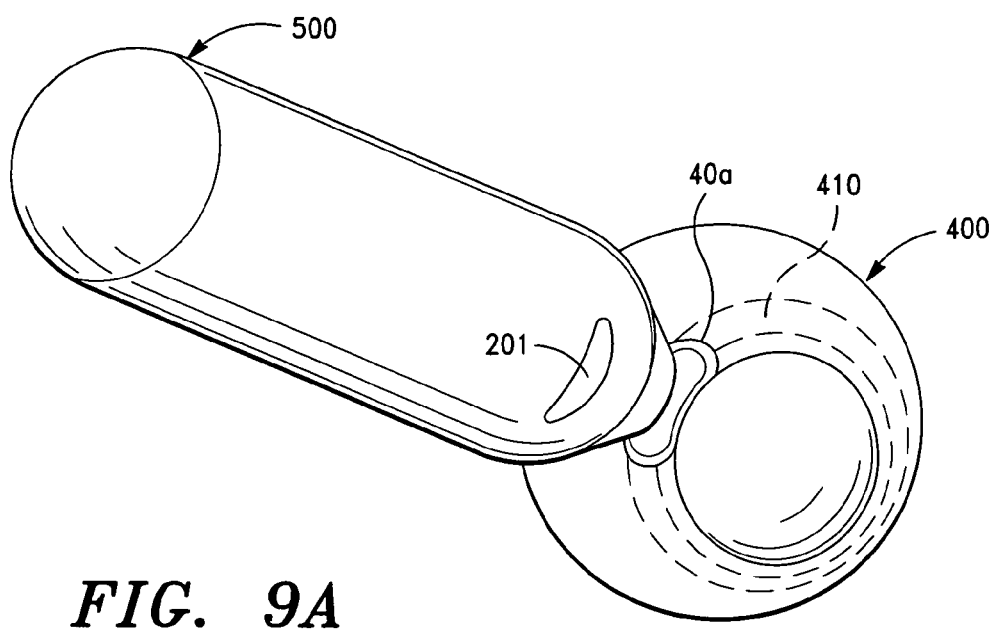
FIGS. 9A-9C are perspective views of an assembled intravitreal injection system applied to the eye, according to the invention.
Figures 9B, 9C:
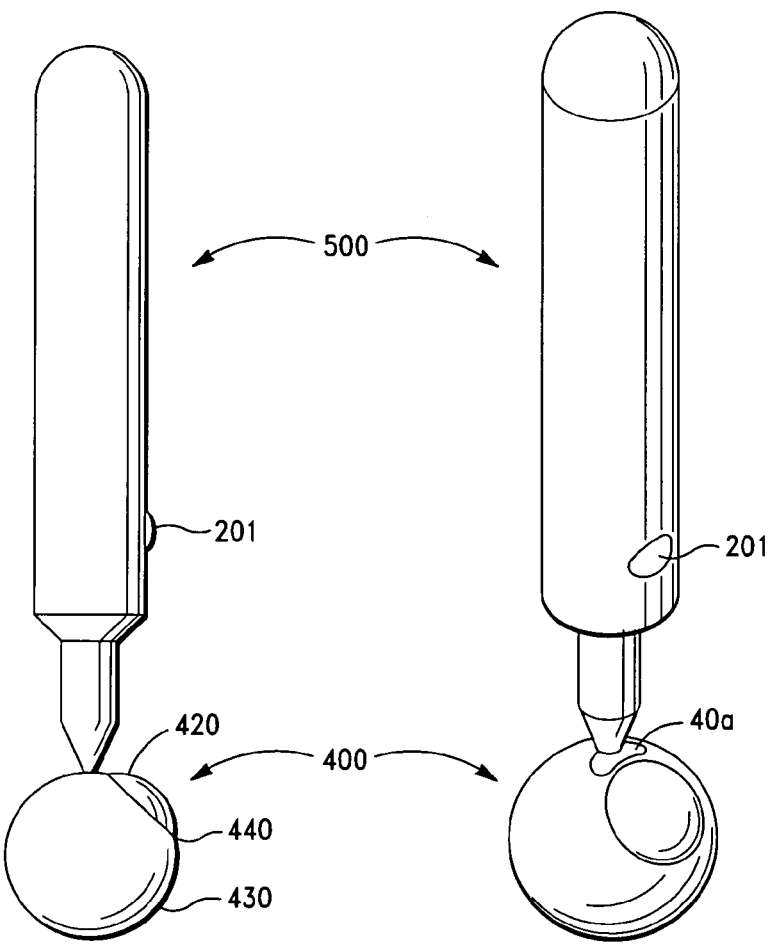

In one embodiment of the invention, precise positioning and application of the microneedle 30 to the pars plana area 410 is accomplished by mating the concave edge of the crescent shaped platform 40a with the junction of the cornea 420 and the sclera 430 or corneoscleral limbus 440 (see FIGS. 9A and 9B).

As indicated above, when a circular platform 40 is employed, the edge of the platform 40 would preferably be placed on the limbus 440. When a star shaped platform 40b is employed, the tip of one of the arms 50 would be placed on the limbus 440.

As noted above, the jet injector 200 is preferably powered by compressed gas, pyrotechnics, electricity, or a spring. In all cases, activation of the jet injector 200 is preferably accomplished by depressing an actuation button 201, which triggers the appropriate power source of the jet injector 200.

In one embodiment of the invention, activation of the jet injector 200 (or power unit thereof) moves a piston 210, which is contained in the power unit 205 of the jet injector 200 (see FIG. 8A), towards the distal end of the injector 200 and, thereby, stopper 105a towards the distal end of the nozzle assembly 300. The pressure generated within the nozzle assembly 300 via the stopper 105a forces the agent formulation through the outlet valve member 110 and into and through the microneedle 30.

Figure 10:
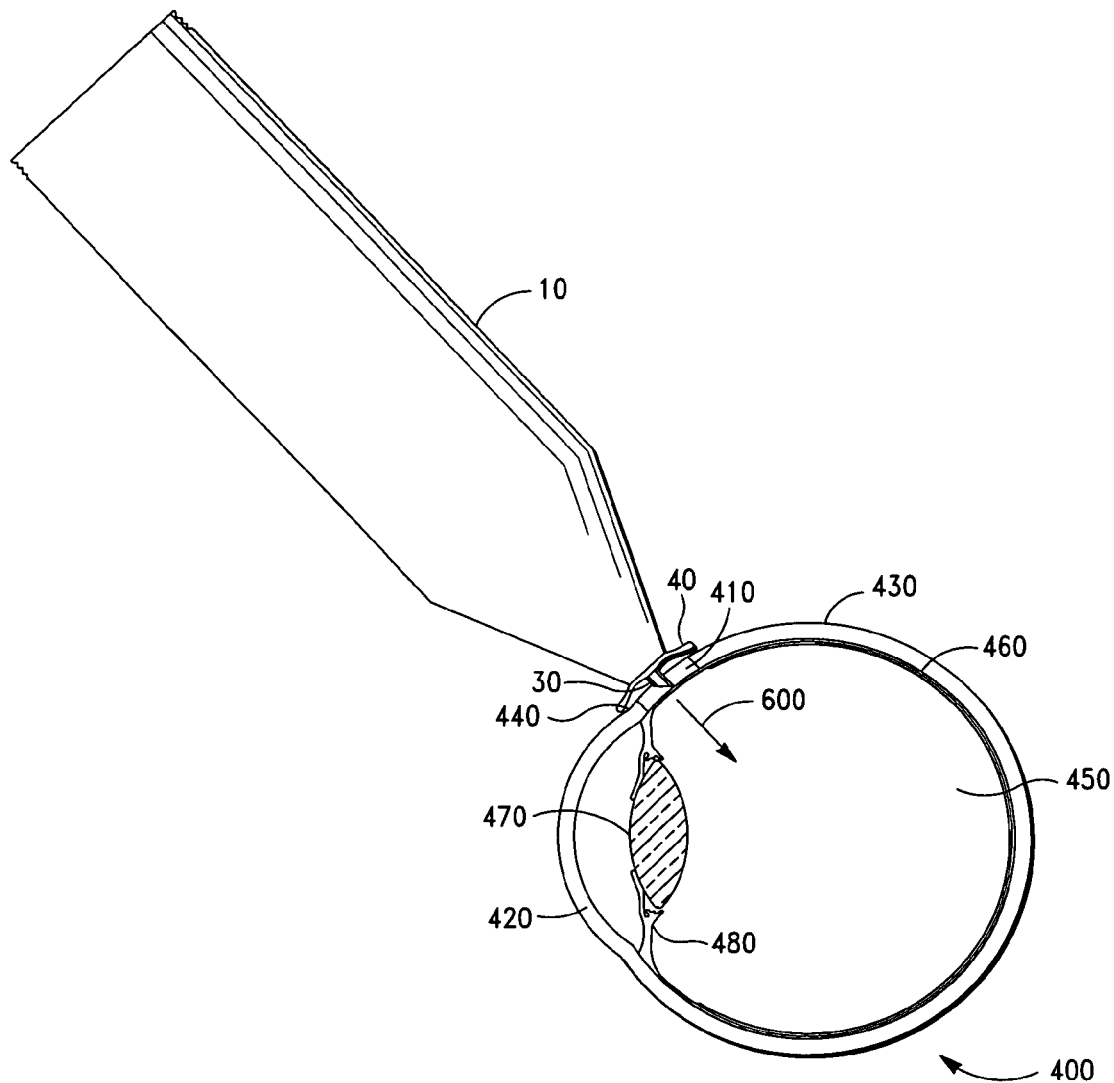
FIG. 10 is a side plane view of one embodiment of a transfer mechanism applied to the eye, according to the invention.

Referring now to FIG. 10, there is shown a cross section of the eye 400 having a transfer mechanism 10 of the invention positioned thereon, i.e. the microneedle 30 being inserted in the pars plana area 410 following positioning of the edge of the platform 40 at the limbus 440. FIG. 10 also illustrates the direction of the agent formulation jet 600 into the vitreous cavity 450. As discussed in detail above, precise positioning of the microneedle 30 and the shallow penetration thereof substantially reduces the risk of injury to major structures of the eye 400, including the retina 460, lens 470, and ciliary body 480.

In another embodiment of the invention (not shown), the jet injector 200 is filled with an agent formulation using an adaptor similar to the adapter disclosed in, for example, U.S. Pat. No. 4,507,113; which is incorporated by reference herein. According to the invention, to administer the required amount of agent formulation, a vial containing the agent formulation is secured in the adapter. The adapter is then coupled to the transfer mechanism, which is preassembled with the jet injector 200. In this embodiment, the stopper 105a is integral part of the injector piston 210.

As indicated above, the jet injector 200 can be a disposable unit, as described in U.S. Pat. No. 6,682,504, and the transfer mechanism 10 can be preassembled thereon and ready for use without any further assembly.

In some embodiments of the invention, the transfer mechanism 10 also includes a removable safety cap at its distal end. In some embodiments of the invention, the transfer mechanism 10 further includes a removable cap at its proximal end.

In some embodiments of the invention, the nozzle member 20 includes a light guide disposed proximate the distal end for precise application to the pars plana portion of the eye.

As will readily be appreciated by one having ordinary skill in the art, the present invention provides numerous advantages compared to prior art methods and systems for administering agents and formulations thereof to the eye. Among the advantages are the following:

The provision of an intravitreal injection method and system that provides safe, accurate, consistent, and rapid injection of therapeutic agents into the intravitreal compartment of the eye.

The provision of an intravitreal injection method and system that facilitates injection of therapeutic agents into the intravitreal compartment of the eye with minimal risk of trauma to the patients' eye by the delivery system.

The provision of an intravitreal injection method and system that facilitates injection of therapeutic agents into the intravitreal compartment of the eye with minimal risk of trauma produced by jet formation inside the eye.

The provision of an intravitreal injection method and system that facilitates injection of agents into the subconjunctival, subtenon spaces or intrascleral and subchoroidal space.

The provision of an intravitreal injection method and system that facilitates injection of therapeutic agents into the intravitreal compartment of the eye with minimal risk of infection to the patient.

The provision of an intravitreal injection method and system that provides semi-automated injection of therapeutic agents into the intravitreal compartment of the eye.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An intravitreal injection system, comprising:
a transfer mechanism, said transfer mechanism including a nozzle member and an integral microneedle-guide platform assembly, said microneedle-guide platform assembly having an integral microneedle and an integral guide platform, said nozzle member having an internal formulation chamber that is adapted to receive and contain a pharmacological agent formulation therein, said microneedle having a first end that is in communication with said nozzle member and a second ejection end, said guide platform having an eye contact surface and a predetermined degree of flexibility, whereby said guide platform substantially conforms to the surface of the sclera of an eye and positions said microneedle-guide platform assembly proximate the pars plana area of said eye when in an engagement position thereon, said guide platform further having a lumen disposed centrally thereof that is adapted to receive and guide said microneedle therethrough and into an intravitreal compartment of an eye and suction means that provides an eye engagement force and seals said guide platform to said pars plana area of said eye when said guide platform is in said engagement position,
said microneedle-guide platform assembly including anchoring means for anchoring said microneedle in said intravitreal compartment of said eye and microneedle piercing depth means for controlling the penetration depth of said microneedle into said intravitreal compartment of said eye to a range of approximately 0.1-1.0 mm when in said engagement position; and
a jet injector having force generating means that is adapted to generate sufficient force to expel said pharmacological agent formulation from said nozzle member and through said microneedle with an injection pressure in the range of approximately 50-1000 psi.

2. The system of claim 1, wherein the volume of said pharmacological agent formulation is in the range of approximately 0.025-0.2 ml.

3. The system of claim 1, wherein said guide platform comprises an elastic, biocompatible polymeric material.

4. The system of claim 1, wherein said guide platform has a substantially circular shape.

5. The system of claim 1, wherein said guide platform has a substantially crescent shape, said crescent shaped guide platform having first and second ends, a convex edge, and a concave edge.

6. The system of claim 5, wherein said microneedle is positioned substantially orthogonal to a plane defined by said crescent shaped guide platform first and second ends.

7. The system of claim 5, wherein said ejection end of said microneedle is directed towards said crescent shaped guide platform convex edge at an angle <30°.

8. The system of claim 1, wherein said guide platform is substantially star shaped, said star shaped guide platform having a plurality of arms.

9. The system of claim 1, wherein said suction means comprises a plurality of suction cups disposed on said guide platform eye contact surface.

10. The system of claim 1, wherein said suction means comprises at least one suction ring disposed on said guide platform eye contact surface.

11. The system of claim 1, including a formulation cartridge that is adapted to contain said pharmacological agent formulation, said cartridge being adapted to be slideably received in said internal formulation chamber of said nozzle member.

12. An intravitreal injection device for administering a pharmacological agent formulation to an intravitreal compartment of an eye, comprising:
  a nozzle member having an internal formulation chamber that is adapted to receive and contain the pharmacological agent formulation therein;
  an integral microneedle-guide platform assembly, said microneedle-guide platform assembly having an integral microneedle and an integral guide platform, said microneedle having a first end that is in communication with said nozzle member and a second ejection end, said guide platform having a lumen disposed centrally thereof that is adapted to receive and guide said microneedle therethrough, said guide platform further having an eye contact surface and a predetermined degree of flexibility, whereby said guide platform substantially conforms to the surface of the scleral membrane of an eye and positions said microneedle and guide platform assembly proximate the pars plana area of said eye when in an engagement position thereon,
  said integral microneedle-guide platform assembly including microneedle guide means for guiding said microneedle into said scleral membrane of said eye, anchoring means for anchoring said microneedle in said scleral membrane at said pars plana area of said eye, controllable microneedle piercing depth penetration means for limiting the penetration depth of said microneedle into said scleral membrane of said eye, and suction means disposed on said guide platform eye contact surface that provides an eye engagement force and seals said microneedle-guide platform assembly to said pars plana area of said eye when said microneedle-guide platform assembly is in an engagement position on said eye.

13. The device of claim 12, wherein said device is adapted to engage and cooperate with a jet injector, said jet injector having force generating means that is adapted to generate sufficient force to expel the pharmacological agent formulation from said nozzle member and through said microneedle.

14. The device of claim 12, wherein said guide platform comprises an elastic, biocompatible polymeric material.

15. The device of claim 12, wherein said guide platform has a substantially circular shape.

16. The device of claim 12, wherein said guide platform has a substantially crescent shape.

17. The device of claim 12, wherein said guide platform is substantially star shaped.

18. The device of claim 12, wherein said suction means comprises a plurality of suction cups.

19. The device of claim 12, wherein said suction means comprises at least one suction ring.

20. A method for administering a pharmacological agent formulation to an intravitreal compartment of an eye, comprising the steps of:
  providing an intravitreal injection system having a transfer mechanism and a jet injector, said transfer mechanism including a nozzle member and an integral microneedle-guide platform assembly, said microneedle-guide platform assembly having an integral microneedle and an integral guide platform, said nozzle member containing the pharmacological agent formulation in an internal formulation chamber, said microneedle having a first end that is in communication with said nozzle member and a second ejection end, said guide platform having an eye contact surface and a predetermined degree of flexibility, whereby said guide platform substantially conforms to the surface of a sclera of the eye when in an engagement position thereon, said guide platform further including suction means that provides an engagement force when said guide platform is in said engagement position on the eye, said guide platform further having a substantially crescent shape that includes a concave edge and a centrally located lumen that is adapted to receive said microneedle and guide said microneedle into said eye when said guide platform is in said engagement position on said eye, said microneedle-guide platform assembly providing a predetermined microneedle penetration depth into said eye in the range of approximately 0.1-1.0 mm when in said engagement position, said jet injector having force generating means that is adapted to generate sufficient force to expel the pharmacological agent formulation from said nozzle member and through said microneedle;
  coupling said intravitreal injection system to said jet injector, whereby an intravitreal injection assembly is formed;
  positioning said intravitreal injection assembly on the pars plana area of the eye by mating said concave edge of said crescent shaped platform proximate the junction of the cornea and sclera of the eye; and
  activating said injector, whereby the pharmacological agent formulation is expelled from said nozzle member, through said microneedle and into the intravitreal compartment of the eye.

21. The method of claim 20, wherein said intravitreal injection assembly is positioned on the pars plana area of the eye by mating said concave edge of said crescent shaped platform proximate the junction of the cornea and corneoscleral limbus of the eye.

22. The method of claim 20, wherein the volume of said pharmacological agent formulation is in the range of approximately 0.025-0.2 ml.

23. The method of claim 20, wherein said jet injector provides an injection pressure in the range of approximately 50-1000 psi.

* * * * *